United States Patent [19]

Epley

[11] Patent Number: 4,628,907

[45] Date of Patent: Dec. 16, 1986

[54] DIRECT CONTACT HEARING AID APPARATUS

[76] Inventor: John M. Epley, 6371 SE. Yamhill, Portland, Oreg. 97215

[21] Appl. No.: 592,236

[22] Filed: Mar. 22, 1984

[51] Int. Cl.[4] .......................... A61B 5/02; H04R 25/00
[52] U.S. Cl. ....................................... 128/1.6; 389/68.3
[58] Field of Search .................... 128/1 R; 179/107 R, 179/107 E, 107 BC

[56] References Cited

U.S. PATENT DOCUMENTS

| | | | |
|---|---|---|---|
| 3,061,689 | 10/1962 | McCarrell et al. | 179/107 |
| 3,346,704 | 10/1967 | Mahoney | 179/107 |
| 3,385,937 | 5/1968 | Lafon | 179/107 |
| 3,439,128 | 4/1969 | Sobel et al. | 179/107 |
| 3,497,637 | 2/1970 | Puharich et al. | 179/107 |
| 3,594,514 | 7/1971 | Wingrove | 179/107 R |
| 3,629,521 | 12/1971 | Puharich et al. | 179/107 R |
| 3,712,962 | 1/1973 | Epley | 179/107 R |
| 3,751,605 | 8/1973 | Michelson | 179/107 R |
| 3,752,939 | 8/1973 | Bartz | 179/107 R |
| 3,764,748 | 10/1973 | Branch | 179/107 E |
| 3,812,300 | 5/1974 | Brander | 179/107 R |
| 3,832,580 | 8/1974 | Yamamuro et al. | 310/9.5 |
| 3,870,832 | 5/1975 | Fredrickson | 179/107 E |
| 3,875,932 | 4/1975 | Wachspress | 128/24 R |
| 3,950,719 | 4/1976 | Maxwell | 335/205 |
| 3,954,101 | 5/1976 | Wachspress | 128/24 R |
| 4,020,298 | 4/1977 | Epley et al. | 179/175 |
| 4,025,734 | 5/1977 | Aloupis | 179/156 R |
| 4,060,701 | 11/1977 | Epley | 179/175 |
| 4,063,048 | 12/1977 | Kissiah | 179/107 R |
| 4,150,262 | 4/1979 | Ono | 179/107 BC |
| 4,204,135 | 5/1980 | Murayama | 310/357 |
| 4,207,441 | 6/1980 | Ricard et al. | 179/107 R |
| 4,261,372 | 4/1981 | Hansen et al. | 128/784 |
| 4,284,085 | 8/1981 | Hansen | 128/784 |
| 4,284,921 | 8/1981 | Lemonon et al. | 310/328 |
| 4,316,115 | 2/1982 | Wilson et al. | 310/327 |
| 4,352,960 | 10/1982 | Dorzer et al. | 179/107 BC |
| 4,369,391 | 1/1983 | Micheron | 310/800 |
| 4,407,389 | 10/1983 | Johnson | 181/135 |

OTHER PUBLICATIONS

Goode et al, "Audition Via Electromagnetic Induction", *Arch Otolarngol,* vol. 98, Jul. 1973, pp. 23 to 26.
Unknown, "Implantable Hearing Aid Project", *Jetro,* Sep. 1982, pp. 6 to 10.

*Primary Examiner*—Edward M. Coven
*Attorney, Agent, or Firm*—Klarquist, Sparkman, Campbell, Leigh & Whinston

[57] ABSTRACT

A direct contact hearing aid apparatus adapted to be mounted deep within the ear canal is disclosed, including an output electromechanical transducer for converting audio output signals into mechanical movement of an output coupling element without the production of discernible sound waves to prevent acoustic feedback. The coupling element is supported in direct contact with a contact element mounted on the tympanic membrane by a metal clip attached to the malleus bone to provide direct electromechanical coupling to the ossicles through the tympanic membrane. The contact element is made of magnetic material, such as a permanent magnet, and is magnetically connected to the coupling element. A pair of magnetic switches are provided within the hearing aid housing for mechanically switching the connections of the battery and a volume control while the hearing aid is mounted in the ear canal in response to changes in the polarity of a remote external magnetic actuator located outside of the housing. An external magnetic insertion probe is used for insertion and removal of the hearing aid into and from the ear canal by magnetic engagement with a magnetic holder member on the housing. The output transducer of the hearing aid may be a piezoelectric plastic film transducer in the form of a flexible diaphragm or a folded sheet bender of the bimorph type, or it may be an electromagnetic transducer. A counterpoise means which may include a weight mounted on a second transducer element that moves in an opposite direction to the output coupling element, is employed to reduce internal vibration of the hearing aid apparatus. A permanent magnet suspension means is employed to support a pivoted motor element of the output transducer connected to the output coupling element for greater resiliency.

15 Claims, 17 Drawing Figures

DIRECT CONTACT HEARING AID APPARATUS

BACKGROUND OF THE INVENTION

The subject matter of the present invention relates generally to hearing aid apparatus and in particular to direct contact hearing aid apparatus mounted in the ear canal with an output transducer having its output coupling element supported to provide direct electromechanical coupling to the ossicles through the tympanic membrane. The coupling element may engage a contact element mounted on the outer surface of the tympanic membrane, and such elements may be a magnet and a magnetic member to provide a magnetic connection. The invention also relates to hearing aid apparatus employing a piezoelectric plastic film as the output transducer and to a magnetic insertion means for insertion and removal of the hearing aid into the ear canal by magnetic engagement with a holder member on the housing of such apparatus. Externally actuated magnetic switch means are provided within the housing for remote mechanical switching of the electrical connections of a battery and volume control means therein.

The present invention is especially useful as a direct contact hearing aid mounted deep within the ear canal of persons who wish to conceal such hearing aid from the view of others. However, such invention is also useful for other types of external hearing aid having its output transducer external to the tympanic membrane, rather than implanted in the middle ear.

Previously it has been proposed to provide a surgically implantable hearing aid employing a piezoelectric output transducer as shown in U.S. Pat. No. 3,712,962 of Epley issued Jan. 23, 1973 and U.S. Pat. No. 3,764,748 of Branch issued Oct. 9, 1973 or an electromagnetic output transducer as shown in U.S. Pat. No. 3,870,832 of Fredrickson issued May 11, 1975 implanted in the middle ear. This has the disadvantage that it requires surgical operations for implantation, repair and change of batteries. If the power supply batteries are not implanted, and are external to the body, they may be connected by electrical contacts extending through the skin to an implanted output transducer, but this is objectionable to many patients.

Conventional external hearing aids in which the input transducer is a microphone and the output transducer is a loudspeaker which modulates an air column between such speaker and the tympanic membrane of the eardrum, have several disadvantages. These disadvantages include acoustic feedback from the loudspeaker to the microphone, inefficient operation resulting in greater power dissipation and frequent battery changes, and distortion of the acoustical output due to a small diameter speaker diaphragm. Previous attempts to overcome acoustical feedback in conventional external hearing aids have included providing an airtight seal in the ear canal in an attempt to acoustically isolate the output transducer loudspeaker deep within the ear canal from the input transducer microphone as shown in U.S. Pat. No. 3,061,689 of McCarrell et al issued Oct. 30, 1962. This has been only partially successful and has not enabled use of maximum gain without feedback. This also has the disadvantage that the airtight mold used as a seal produces an uncomfortable sensation of fullness and increases the perception of internal noises such as one's own voice. In addition, in the McCarrell patent an ear mold containing the microphone, the amplifier and the battery is positioned in the external portion of the ear so that a volume control for such amplifier may be adjusted manually while the hearing aid is in place in the ear. Unfortunately, this requires that the ear mold piece of the hearing aid be located at a position where it can easily be viewed by persons talking to the wearer which is cosmetically objectionable.

Both electromagnetic transducers and piezoelectric transducers are employed as output transducers in McCarrell, but they are not placed in direct contact with the outer surface of the tympanic membrane in the manner of the present invention. Instead, his output transducers are employed as loudspeakers to produce a sound output by vibrating a plastic diaphragm. However, in one embodiment an iron slug is mounted by adhesive directly on the outer surface of the eardrum and spaced away from the electromagnetic transducer core by an air gap whose width would inadvertently vary depending upon the position of the transducer in the ear canal. The width of such air gap is critical to efficiency since it varies with the third power of such width. The appropriate air gap width for maximum efficiency would therefore be very difficult to obtain by positioning the hearing aid in the ear canal and to maintain with any consistency. In addition, the continuous undirectional stress placed on the eardrum membrane by attraction of the magnetic slug toward the electromagnetic pole piece would stress the ossicular chain and tend to weaken and tear the tympanic membrane.

The hearing aid of the present invention eliminates these disadvantages by positioning the output coupling element of the output transducer in direct contact with the outer surface of the tympanic membrane or with a contact element secured to the outer surface of such membrane, thereby eliminating any airspace between the output transducer and the tympanic membrane. As a result, there is direct electromechanical coupling from the output coupling element of the transducer to the ossicle bones through the tympanic membrane without the generation of any discernible sound waves thereby eliminating acoustic feedback, providing a much more efficient operation and greatly reducing distortion. Also, the lack of undirectional stress would prevent damage to the eardrum.

An experimental hearing aid in which a magnet was attached by glue to the outer surface of the tympanic membrane for movement of the magnet by an induced electromagnetic field produced by a coil on the exterior ear is described by Goode et al in "Audition via Electromagnetic Induction" published July 1973 in *Arch Otolaryngol,* Volume 98, pages 23–26. This hearing aid by employing electromagnetic induction coupling for movement of a magnet attached to the tympanic membrane is not practical because of the large amount of power required. Such article also describes earlier unsuccessful experiments by Wilska who attached small pieces of iron on the tympanic membrane for vibration by a coil and superimposed constant magnetic field of a permanent magnet which are placed over the ear canal, but the strong magnetic attraction apparently stretched or tore the eardrum and caused severe discomfort and pain. Wilska apparently also attached a small electromagnetic coil to the tympanic membrane with similar results except that the coil temperature also caused burning and pain. Unlike the present hearing aid, there was no direct electromechanical coupling of the output transducer of the hearing aid into engagement with the outer surface of the tympanic membrane or with a contact element provided on such membrane with all of its advantages of excellent sound fidelity, low power requirements and no pain, stress or damage to the eardrum during operation of the hearing aid.

It is interesting to note that as recently as September 1982 researchers were still attempting to implant hearing aid output transducers, such as piezoelectric ceramic vibrators, in the middle ear in order to overcome the disadvantages of conventional external hearing aids. In this regard, see the summary of Japanese research and development projects in the article "Implantable Hearing Aid Project" published in *Jetro*, September 1982, pages 6 to 10, which discloses a similar hearing aid to that shown in one of the embodiments of the earlier discussed U.S. Pat. No. 3,712,962 of Epley.

It has been previously proposed in U.S. Pat. No. 3,832,580 of Yamamuro et al issued Aug. 27, 1974 and U.S. Pat. No. 4,369,391 of Micheron issued Jan. 18, 1983 to provide a piezoelectric plastic transducer in non-hearing aid devices, such as a phonographic pick-up and pressure sensing cables, made of a piezoelectric plastic film including a natural or synthetic high molecular weight polymers and polyvinylidene fluoride. However, such piezoelectric plastic film has not previous been used in a hearing aid. It has been discovered by the present inventor that the low mechanical vibration impedance of piezoelectric plastic film transducers closely matches that of the middle ear so that it is ideal for use as the output transducer of a hearing aid. This discovery has lead the inventor to develop several different types of piezoelectric plastic film output transducers for hearing aids which are shown herein.

SUMMARY OF INVENTION

It is therefore one object of the present invention to provide an improved hearing aid apparatus for mounting in the ear canal so that the output transducer thereof has its output coupling element in contact with the tympanic membrane or a contact element on the exterior surface of the tympanic membrane to provide direct electromechanical coupling to the ossicle bones through the tympanic membrane for more efficient operation and for concealment from the observer.

Another object of the invention is to provide such a hearing aid in which the output transducer does not produce discernible sound waves, but provides mechanical coupling between the coupling element of the output transducer and the ossicle bones to eliminate acoustical feedback and to provide less distortion of the resulting acoustical output signal for more realistic hearing.

A further object of the invention is to provide such a hearing aid in which the contact element includes a magnetic member which is fastened by a clip to the malleus bone through the tympanic membrane and is held by magnetic attraction into contact with the output coupling element of the output transducer for better mechanical connection without stress or damage to the tympanic membrane and more efficient operation.

An additional object of the invention is to provide such an improved hearing aid in which the output transducer is made of piezoelectric plastic film that provides the electromechanical vibration of the coupling element and has a vibration impedance which more nearly matches that of the ossicular chain of the middle ear for more efficient operation.

Still another object of the invention is to provide such a hearing aid apparatus which may be inserted into and removed from the ear canal more easily by an external magnetic inserter member which may be magnetically attached to a holder member on the hearing aid housing, and which releases such holder member by changing the magnetic polarity of such inserter.

A still further object of the invention is to provide such a hearing aid in which magnetic switches are employed in the housing of the hearing aid to change the connections of a battery in such housing to turn on and off an amplifier therein and to adjust a volume control of the hearing aid by means of an external magnetic actuator while the hearing aid is mounted within the ear canal.

A still additional object of the invention is to provide an improved hearing aid having an output transducer of electromagnetic or piezoelectric type provided with a counterpoise means that may include a counterweight and which moves in an opposite direction to the output transducer to reduce internal vibration.

Another object of the invention is to provide such a hearing aid having an output transducer including a pivoted motor member connected to the output coupling element and which is supported by a permanent magnet suspension system in order to provide a highly resilient support for such coupling element.

A further object of the invention is to provide a hearing aid in which the mechanical coupling element of the output transducer is mounted in a highly resilient manner to avoid increasing the internal impedance of the middle ear sound conduction mechanism to an extent which would increase the user's perception of internal noise.

A still further object of the present invention is to provide such a hearing aid in which the elimination of acoustical feedback and the provision for remote control of power and volume allows the entire hearing aid apparatus to be placed deep within the ear canal for concealment from the observer.

DESCRIPTION OF DRAWINGS

Other objects and advantages of the present invention will be apparent from the following detailed description of several preferred embodiments thereof and from the attached drawings of which.

DESCRIPTION OF PREFERRED EMBODIMENTS

Figures 1, 2, 3, 4, 5:
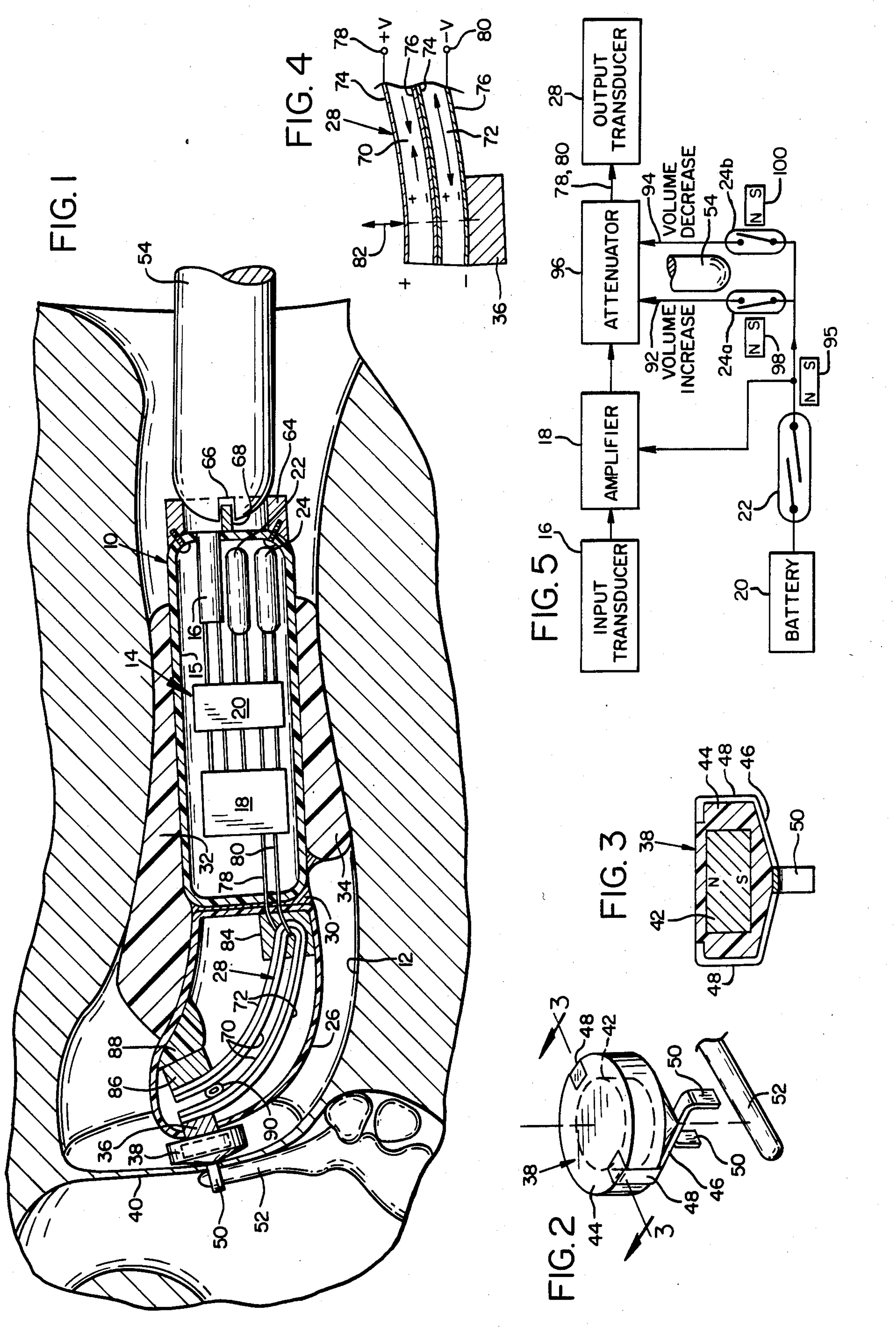
FIG. 1 is a cross-section view of a hearing aid in accordance with one embodiment of the present invention shown mounted within the ear canal so that its output transducer coupling element is in engagement with a contact element mounted on the exterior of the tympanic membrane and attached to the malleus bone, together with a portion of a magnetic inserter for such hearing aid.
FIG. 2 is an enlarged perspective view of the contact element of FIG. 1 mounted on the outer surface of the tympanic membrane before it is attached to the malleus bone.
FIG. 3 is a section view taken along the line 3—3 of FIG. 2.
FIG. 4 is an enlarged partial section view of a portion of the piezoelectric plastic film output transducer employed in the hearing aid of FIG. 1.
FIG. 5 is a block diagram of the electrical circuit of the hearing aid of FIG. 1 showing magnetically actuated switches for controlling the volume and for connecting the battery to the hearing aid in response to an external magnetic actuator.

As shown in FIG. 1 a hearing aid apparatus 10 in accordance with one embodiment of the present invention is adapted to be mounted within the ear canal 12 so that it cannot be seen by a casual observer. The hearing aid 10 includes a main electrical circuit portion 14 contained within a main housing 15. The main circuit 14 includes a microphone input transducer 16, an amplifier 18 and a battery 20. The amplifier includes a digital attenuator volume control that may be of the type shown in my earlier U.S. Pat. No. 4,020,298 of Epley et al issued Apr. 26, 1977 and both can be formed on a single integrated circuit chip as a solid state amplifier and digital attenuator. In addition, the main circuit 14 also includes a pair of magnetic switch means 22 and 24 which, respectively, function as an on/off switch for the battery and as a volume control switch for adjusting the amplitude of the output signal of the hearing aid, in a manner hereafter discussed.

An output housing 26 is attached to the main housing and contains an output transducer 28 electrically connected to the output of the amplifier 18. The output housing 26 may be made of flexible plastic material suitably secured to the main housing 15 of more rigid plastic material by a suitable adhesive 30. A pair of cushions 32 and 34 of polyurethane foam or other resilient elastomer material are also secured to the outer surface of the main housing 15 in any suitable manner, such as by gluing. However, it is also possible to make the main housing 15 solid rather than hollow, so that the main circuit components are embedded in soft plastic and the cushions 32 and 34 are formed integral therewith. The cushion members 32 and 34 which may be custom molded to the shape of the wearer's ear engage the surfaces of the ear canal 12 to hold the hearing aid snugly within the ear canal in a position so that an output coupling element 36 attached to the output transducer 28 is in engagement with a contact element 38 mounted on the outer surface of the tympanic membrane 40. Alternatively, the output coupling element 36 may be placed in direct contact with the outer surface of the tympanic membrane.

The contact element 38 is shown in greater detail in FIGS. 2 and 3 and includes an insert cylinder 42 of magnetic material, such as a permanent magnet, embedded in a cylindrical button 44 of suitable plastic material having a conical bottom surface which engages the outer surface of membrane 40. The button 44 is mounted on a metal clip 46 of platinum, tantalum or other inert metal. The clip 46 includes a pair of holder arms 48 which engage notches in the opposite sides of the button 44 to hold the contact element 38 and a pair of mounting legs 50 which are bent around the end of the malleus bone 52 after passing through the tympanic membrane to mount such contact element on the outer surface of such membrane. Thus, mechanical movement of the coupling element 36 by the output transducer 28 in response to the output signal of the hearing aid is directly coupled to the contact element 38 and through the tympanic membrane 40 to the malleus bone 52 of the ossicular chain in the preferred embodiment of the present invention. However, it is also possible to attach the contact element 38 by adhesive to the outer surface of the tympanic membrane 40 or to engage such membrane directly with the output coupling element 36. The output coupling element 36 is a cylindrical or rectangular block of ferromagnetic material, such as soft iron, which is attached to the output transducer 38 in any suitable manner such as by glue. This output coupling element is magnetically attracted by the permanent magnet insert 42 into engagement with the contact element 38 when the hearing aid apparatus 10 is mounted within the ear canal 12 in the operating position shown in FIG. 1.

Figure 6:
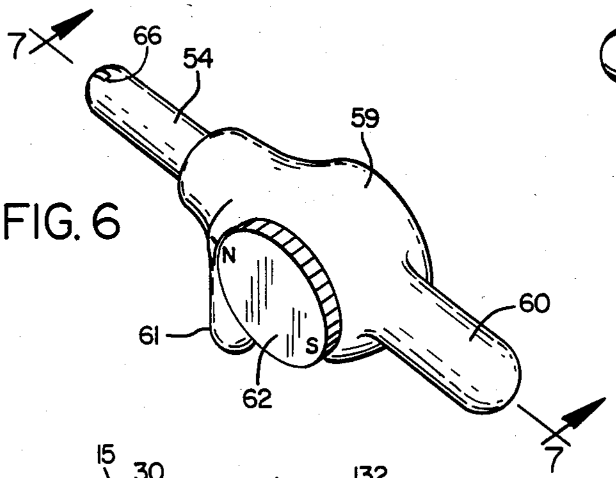
FIG. 6 is a perspective view of a magnetic inserter device for insertion and removal of the hearing aid apparatus of FIG. 1 which is also used as a magnetic actuator for actuation of the switches of FIG. 5.
Figure 7:
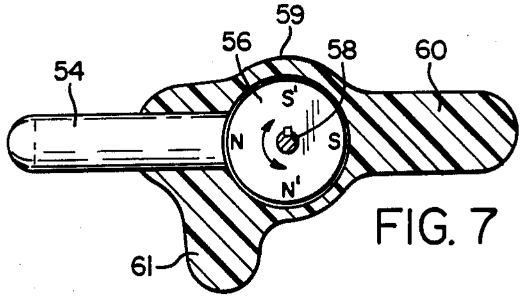
FIG. 7 is a section view taken along the line 7—7 of FIG. 6 showing the rotatable permanent magnet member within the inserter.

Insertion and removal of the hearing aid apparatus is accomplished by a magnetic inserter including a probe rod 54 which is shown in greater detail in FIGS. 6 and 7. The magnetic inserter probe 54 is a rod of ferromagnetic material which is mounted in contact with a rotatable permanent magnet 56 in the shape of a cylinder with its central axis perpendicular to its magnetic polar axis, that rotates about the axis of rotation of a mounting pin 58 keyed to such magnet to hold the magnet within a molded plastic housing 59. The housing of the inserter has a handle portion 60 and a stop portion 61 which engages the outer ear to limit the depth of penetration of the rod 50 within the ear canal. The magnet 56 is rotated by an adjustment dial 62 fixed to pin 58 in order to orient the north pole (N) or south pole (S) of the magnet 56 into contact with the end of the inserter rod 54 at different times. As a result, the polarity of the magnetic attraction at the outer end of such rod may be changed. The outer end of rod 54 is placed in engagement with a magnetic holder ring 64 of soft iron or other ferromagnetic material for magnetic attachment to enable insertion and removal of the hearing aid. The holder ring 64 is secured to the upper end of the main hearing aid housing 14 by rivets, screws, epoxy resin adhesive or any other suitable fastening technique. An orientation slot 66 may be provided in the end of the inserter rod 54 for engagement with an orientation bar 68 extending across the diameter of the holder ring 64 as shown in FIG. 1. This orientation means is necessary in order to orient the hearing aid apparatus in a proper rotational position of the rod 54 so that the output coupling element 36 is aligned with the contact element 38 during insertion of the hearing aid into the ear canal.

After insertion is completed, the knob 62 is rotated 90° from the initial position N and S of its magnetic poles to locate the magnetic poles at the positions N′ and S′ shown in FIG. 7. This eliminates the magnetic attraction of the insertion probe rod 54 to release such rod from the holder ring 64 and thereby enables withdrawal of the inserter from the ear canal while leaving the hearing aid located in the position shown in FIG. 1. Withdrawal of the hearing aid apparatus from the ear canal is accomplished by rotating the magnet 56 back into the position shown in FIG. 7 and then inserting the probe 54 until its slot 66 engages the orientation bar 68 and moves down into contact with the magnetic holder ring 64. Then the inserter 54 is withdrawn from the ear canal while it is magnetically attached to the hearing aid, thereby pulling the hearing aid from the canal. It should be noted that the orientation of the magnetic pole at the outer end of the inserter 54 is such that it opposes the upper magnetic pole of the insert magnet 42 of the contact element 38, thereby releasing the coupling element 36 from such contact element. Thus, with the magnetic insert 42 having the north/south pole polarity indicated in FIG. 3, for connection release and removal a north pole is provided at the slotted end 66 of the inserter probe 54.

The output transducer 28 is preferably made of piezoelectric plastic film and may be a bimorph piezoelectric transducer formed of two layers 70 and 72 of piezoelectric plastic film, such as a polyvinylidene fluoride (PVDF) manufactured by Pennwalt Corporation and sold under their tradename KYNAR. Each of the two piezoelectric film layers 70 and 72 is provided with a pair of metalized surfaces forming upper and lower contacts 74 and 76 on opposite sides thereof. The piezoelectric layers 70 and 72 are oriented so that the major axis of contraction and expansion of each are parallel to the other, but the electrical poling axis of one is oriented relative to the other so that one layer contracts as the other expands and visa versa as shown in FIG. 4. Thus, when a positive voltage (+V) is applied to the upper contact 74 of piezoelectric layer 70 and a negative voltage (−V) is applied to the lower contact 76 of layer 72 current flows downward through such layers causing the upper layer 70 to contract as indicated by the two arrows pointing toward each other and the lower layer 72 to expand as indicated by the two arrows pointing away from each other. This simultaneous contraction of layer 70 and expansion of layer 72 causes the bimorph transducer 28 to bend upward, thereby mechanically deflecting the coupling element 36 of ferromagnetic material which is secured to the end of the transducer as shown in FIG. 4. Of course, when the polarity of the output signal changes so a negative voltage is applied to contact 74 and positive voltage applied to contact 76 of layers 70 and 72, respectively, the direction of current flow through such layers reverses and the transducer bends downward. Output leads 78 and 80 attached to the outputs of the amplifier 18 are electrically connected to the contact layers 74 and 76 of the two piezoelectric layers 70 and 72, respectively, in order to cause bending movement of the output transducer and the coupling element 36 attached thereto toward and away from contact element 38 in the direction of arrows 82.

The output transducer 28 may be a sheet of bimorph piezoelectric film which is folded in the center to form a bender transducer with two spaced arms and is fixedly secured to housing 26 at its central portion by a suitable plastic material, such as epoxy resin, to provide a fixed anchor base 84 which is attached to the top end of the output housing 26. The amplifier output leads 78 and 80 are soldered to contacts 74 and 76 and embedded in the plastic anchor base 84 to prevent movement of such leads. The resulting piezoelectric bender transducer has its upper arm attached to a counterpoise weight 86 of lead or other suitable metal secured thereto by glue for movement with such upper arm as a counterpoise in a direction opposite to that of the coupling element 36 attached to the lower arm of such bender element. The counterpoise weight 86 is also resiliently secured to the output housing 26 by a resilient plastic foam 88 such as polyurethane for dampening purposes. Thus, the upper arm of the piezoelectric bender and its weight 86 together with the resilient foam mounting 88 reduce internal vibrations when the lower arm of the bender and the coupling element 36 attached thereto are moved in response to the receipt of an output signal on leads 78 and 80 from the hearing aid amplifier 18. A resilient spacer 90 which may be made of hollow tubing of rubber or other elastomer may be positioned between the two arms of the bender transducer 28 in order to further dampen the vibration of such arms and to maintain the proper spacing between such arms.

It should be noted that the coupling element 36 extends through an aperture in the output housing 26 into engagement with the upper surface of the contact element 38 in alignment with the insert magnet 42. Thus, moisture could enter the output housing 26 but will have no effect on the operation of the hearing aid because all exposed electrical connections are within the main housing 15 which is sealed. The input end of microphone 16 may extend through an aperture in the main housing 14 of the hearing aid to better receive sound wave signals transmitted through the ear canal, but its electrical connections are not exposed. Also, it is possible that the output transducer 28 of FIG. 1 will work if the upper arm and counterweight 86 attached thereto are eliminated. However, this is not desirable because of their counterpoise function which reduces vibration.

The electrical circuit for the hearing aid 10 is shown in FIG. 5 and includes a magnetic microswitch 22 connected between the D.C. power supply battery 20 and the amplifier 18 so that such battery is not connected to the amplifier until such switch is closed. This is accomplished by an external magnetic actuator which can be provided by the magnetic inserter of FIGS. 6 and 7. Thus, the magnetic microswitch 22 may be a latching type of reed switch with a bias magnet 95 that is biased open and is closed only when an external magnetic field of sufficient strength is applied thereto and remains closed until again magnetically actuated, like a push button type switch. Another suitable magnetic switch is shown in U.S. Pat. No. 3,950,719 of Maxwell issued Apr. 13, 1976. When the north or south pole of the magnet cylinder 56 is in engagement with the probe rod 54 and such probe rod is moved near the holder ring 64, switch 22 is actuated. The output terminal of switch 22 is also connected through a pair of volume control switches 24A and 24B which may be magnetic reed switches that are more sensitive than switch 22 to an external magnetic field and have their movable contacts normally biased open and connected in common to the same input terminal. However, the fixed contacts of the magnetic switches 24A and 24B are connected to different control terminals 92 and 94 of a digital attenuator circuit 96 of the type shown in FIG. 3B of my U.S. Pat. No. 4,020,298 of Epley issued Apr. 26, 1977. Thus, when switch 24A is closed connecting control terminal 94 to the battery 20, the attenuator resistance decreases slowly so there is a volume increase and when switch 24B is closed to connect control terminal 94 to such battery, the attenuator resistance increases slowly so there is a volume decrease. The magnetic switches 24A and 24B are selectively actuated one at a time by changing the magnetic polarity of the actuator rod 54 between north and south. This is accomplished by providing a first bias magnet 98 adjacent the reed switch 24A whose inner end is of an opposite polarity to the inner end of a second bias magnet 100 positioned adjacent the reed switch 24B. Thus, in the position shown of the bias magnets 98 and 100, such bias magnets normally bias the magnetic switches 24A and 24B, respectively, to attract their movable contacts outward into the open positions shown. When the magnetic actuator probe 54 is positioned adjacent the switches 24A and 24B on the opposite sides of the switches from the bias magnets, a north magnetic pole on such probe will close switch 24B and will leave switch 24A open, while a south pole on such probe will close switch 24A and leave switch 24B open. The magnetic polarity of the actuator probe 54 is changed from north to south by rotation of the magnet cylinder 56 through 180°. In this manner, the magnetic switches 24A and 24B may be selectively actuated by moving the actuator rod 54 toward holder ring 64 for applying an external magnetic field to close one of the switches which is less than the field strength required to operate switch 22. It is obvious that the switches 22, 24A and 24B may be actuated by any external magnetic actuator, not merely that shown.

Figure 9:
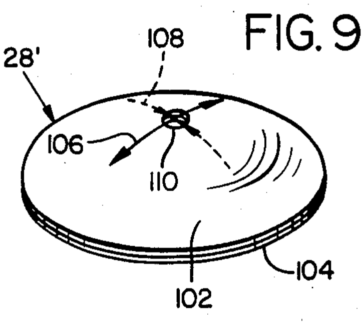
FIG. 9 is a perspective view showing the flexing movement of the piezoelectric diaphragm used in FIG. 8.
Figure 8:
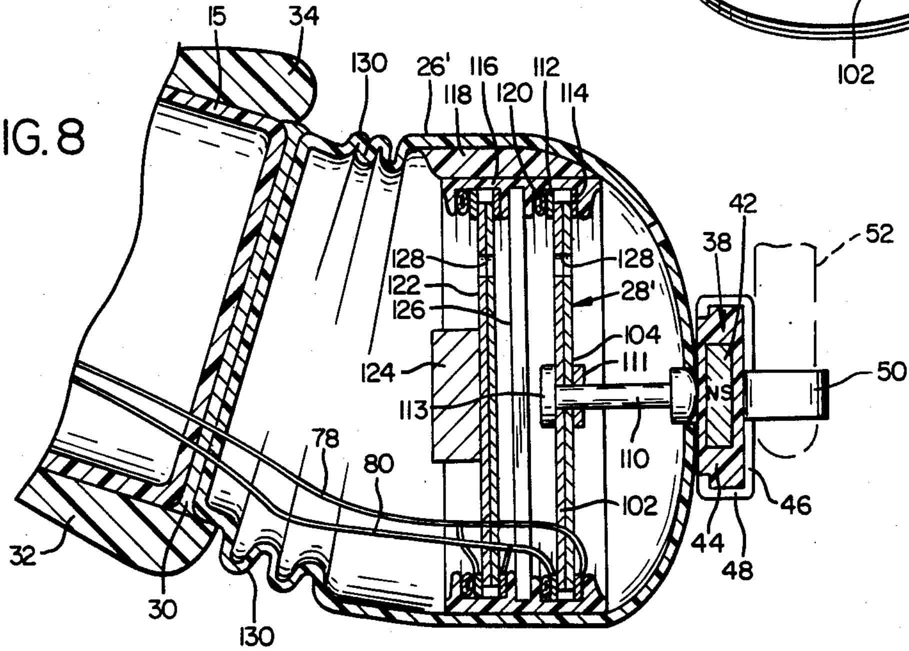
FIG. 8 is a partial section view of a second embodiment of the hearing aid apparatus of the present invention with a different output transducer than that of FIG. 1 including a piezoelectric plastic diaphragm connected to the output coupling element of such transducer.

As shown in FIGS. 8 and 9, a second embodiment of the hearing aid of the present invention is similar to that of FIG. 1, but employs a different piezoelectric output transducer 28' in the form of a bimorph piezoelectric plastic diaphragm. The diaphragm output transducer includes a first piezoelectric layer 102 and a second piezoelectric layer 104 of annular disc shape which are bonded together by an electrically conductive adhesive to form a diaphragm which flexes up and down in response to the application of output signals thereto by output leads 78 and 80 of the amplifier 18 (not shown). The two piezoelectric plastic film layers 102 and 104 have metalized outer surfaces similar to contacts 74 and 76 of the bending bimorph transducer of FIG. 4 which are in contact with leads 78 and 80. However, the inner surfaces of the layers 102 and 104 are also provided with metalized films which contact one another through the electrically conductive adhesive so that such layers are electrically connected in series. The major axis 106 of contraction and expansion of the upper layer 102 is orientated at 90° with respect to the major axis 108 of expansion and contraction of the lower layer 104 as shown in FIG. 9 and is of opposite polarity so one layer expands while the other layer contracts in order to provide three-dimensional hemispherical bending deflection of the diaphragm transducer of FIGS. 8 and 9, rather than the two-dimensional bending achieved by the bender transducer of FIGS. 1 and 4.

A coupling element 110 in the form of a rod of soft iron or other magnetic material is attached to the transducer diaphragm in any suitable manner such as by clamping between an annular flange 111 and a threaded ring 113 on the inner end of the rod so it extends through an aperture in the center of the piezoelectric discs 102 and 104. Such diaphragm layers 102 and 104 may be of a piezoelectric plastic film material similar to that described above with respect to layers 70 and 72 of FIGS. 1 and 4. An enlarged outer end of the output coupling element 110 extends through an aperture in the flexible plastic output housing 26' surrounding the output transducer so that such enlarged end is positioned in engagement with a contact element 38 mounted on the outer surface of the tympanic membrane by the clip 46 whose mounting arms 50 are attached to the malleus bone 52 in a similar manner to that of FIG. 1. Thus, the coupling element 110 couples the deflection of the output transducer diaphragm 28' to the contact element 38 which moves the tympanic membrane and the malleus bone 52 in response to the output signal of the hearing aid amplifier.

The inner end of the coupling rod 110 is suitably secured by clamping and/or gluing to the piezoelectric diaphragm layers 102 and 104 for movement with such diaphragm. A pair of metal contact rings 112 and 114 are provided on opposite sides of the diaphragm adjacent the outer edges thereof to make electrical contact with the metal contact surfaces on layers 102 and 104 corresponding to the contact surfaces 74 and 76 in FIG. 4, while enabling sliding movement of the edges of the piezoelectric layers during flexing. The leads 78 and 80 for the diaphragm transducer are electrically connected to such metal rings. The metal rings 112 and 114 are held within an annular mounting notch in a support rack 116 of rigid plastic which is suitably secured to the inner surface of the flexible output housing 26' by glue 118. A rubber O-ring 120 is positioned between the metal contact rings and one of the pair of projections on the rack 116 forming the mounting notch for the transducer diaphragm for resiliently urging such rings into engagement with the diaphragm contact surfaces.

A second piezoelectric plastic bimorph diaphragm transducer 122 of similar construction to the output transducer diaphragm 28' may also be mounted on the support rack 116 in a similar manner but spaced therefrom. The piezoelectric layers of the bimorph transducer 122 are connected to leads 78 and 80 in an opposite polarity to the output transducer diaphragm 28' so that such transducer diaphragm flexes an equal amount but in opposite direction to that of the output transducer diaphragm. As a result, diaphragm 122 functions as a counterpoise to reduce vibration of the hearing aid housing. In this regard, a counterpoise weight 124 of heavy metal, such as lead, is suitably secured by glue to the upper surface of the diaphragm 122 to further dampen vibration. A stop bar or disc 126 of metal is mounted between the output transducer diaphragm 28' and the counterpoise diaphragm 122 in a third slot provided in the mounting rack 116 to limit the deflection of the output transducer diaphragm 28' and the counterpoise diaphragm 122 to prevent damage to the diaphragms. A plurality of vent holes 128 are provided in each of the diaphragms 28' and 122 for enabling air to pass through such diaphragms to minimize the production of air borne sound waves. Also, it should be noted that the output housing 26' is provided with folds 130 for greater flexibility to enable the axis of the coupling rod 110 to be adjusted to form an included angle between about 135° and 180° with respect to the longitudinal axis of the main housing 15 depending upon the shape of the ear canal of the wearer.

Figure 11:
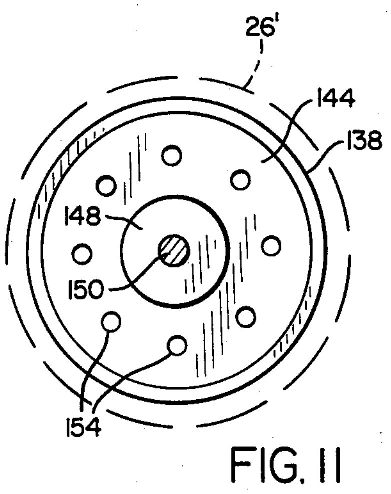
FIG. 11 is a section view taken along the line 11—11 of FIG. 10 showing the flexible diaphragm.
Figure 10:
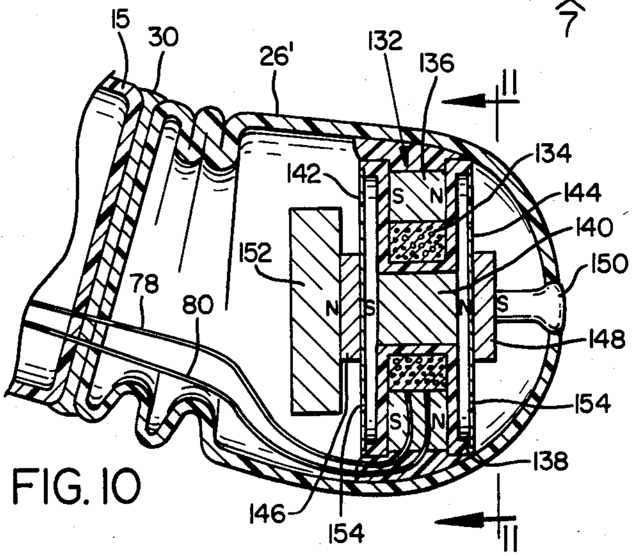
FIG. 10 is a partial section view of a third embodiment of the present invention employing an electromagnetic output transducer with a fixed coil for movement of the output coupling element mounted on a flexible diaphragm.

A third embodiment of the hearing aid apparatus of the present invention is shown in FIGS. 10 and 11 which is similar to that of FIG. 1, but employs an electromagnetic output transducer 132. Such output transducer includes a fixed electromagnetic coil 134 electrically connected by leads 78 and 80 to the outputs of the amplifier 18 in the main housing 15. The coil is surrounded by an annular permanent magnet 136 and are both fixedly mounted within a spool 138 of nylon or other rigid plastic having a central aperture containing an iron core 140 fixedly attached thereto. A pair of resilient flexible plastic diaphragms 142 and 144 are suitably secured, such as by gluing at their outer edges, across the ends of the plastic spool 138 and spaced therefrom sufficiently to enable deflection of such diaphragms. Unlike the embodiment of FIG. 8, the plastic diaphragms 142 and 144 are not made of piezoelectric plastic material, but conventional high-strength resilient plastic such as Mylar. A pair of permanent magnets 146 and 148 are secured to the outer surfaces of the plastic diaphragms 142 and 144, respectively, such as by gluing. As a result of the magnetic field produced by the electromagnetic coil 134 and the magnetic flux produced in the iron core 40, the permanent magnets 146 and 148 are deflected toward and away from such core along with the diaphragms 142 and 144 connected thereto in response to an output signal applied to coil 134 by leads 78 and 80 from the amplifier 18 (not shown).

Permanent magnet 148 is connected to an output coupling element 150 of steel or other ferromagnetic material which extends through an aperture in the output housing 26' into engagement with the contact element 38 in a similar manner to that of FIG. 8. As a result, the electromagnetic output transducer 132 provides mechanical movement of the output coupling element 150 by deflection of the diaphragm 144 in response to the receipt of output signals of the hearing aid amplifier. A counterpoise weight 152 is attached to the permanent magnet 146 on the other diaphragm 142 in a suitable manner, such as by gluing, and is deflected up and down by the flexing of such other diaphragm. However, it should be noted that because of the polarity of the permanent magnets 146 and 148, the diaphragm 142 and counterpoise weight 152 are deflected in a direction opposite to the movement of the transducer output coupling element 150 and its associated diaphragm 144, thereby functioning as a counterpoise to reduce internal vibration. A plurality of vent openings 154 may be provided in each of the diaphragms 142 and 144 to enable air to pass through to minimize the production of air borne sound waves as shown in FIG. 11.

Figure 12:
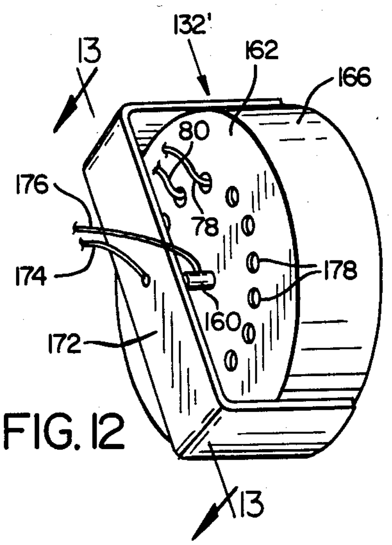
FIG. 12 is a partial perspective view showing a fourth embodiment of the present invention having an electromagnetic output transducer with a moving electromagnetic coil attached to the coupling element which is supported on flexible diaphragms and including an overload sensor contact for sensing when there is too much deflection of the coupling element and signaling that the volume control must be adjusted to reduce the amplitude of the output signal applied to the coil.
Figure 13:
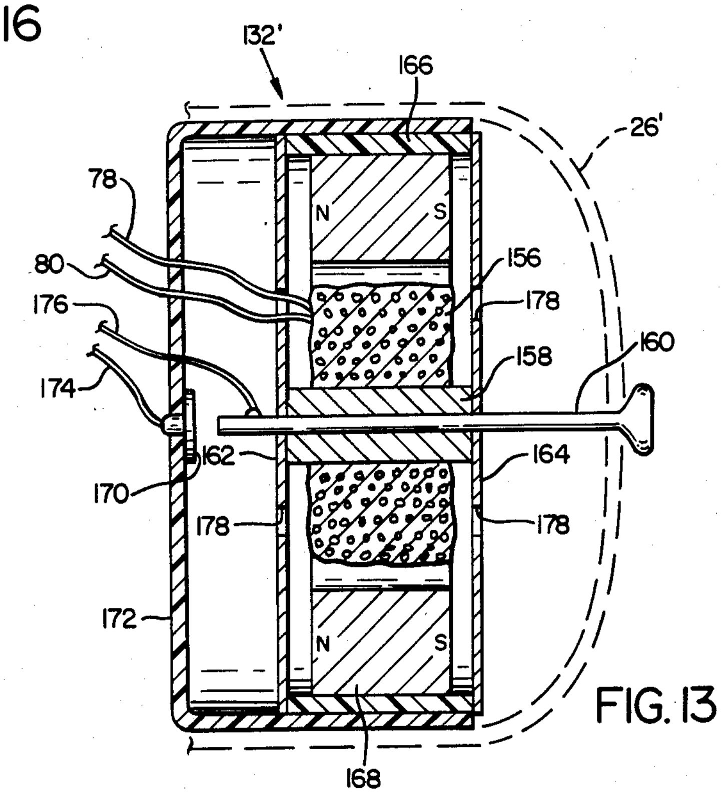
FIG. 13 is an enlarged section view taken along the line 13—13 of FIG. 12.

The fourth embodiment of the hearing aid of the present invention is shown in FIGS. 12 and 13 which is similar to FIGS. 1 and 10, but employs another type of electromagnetic output transducer 132' including a moving electromagnetic coil 156. Such coil is attached to the outer surface of a moving magnetic core tube 158 of ferromagnetic material through which an output coupling rod 160 of steel or ferrous metal extends which is fixedly secured thereto. The core 158 is attached by glue or clamping at its opposite ends to a pair of flexible diaphragms 162 and 164 for movement therewith. The diaphragms 162 and 164 are made of a non-piezoelectric resilient flexible plastic, such as Mylar, and are secured by glue at their outer edges to a fixed mounting ring 166 of nylon or other suitable rigid plastic material. A fixed permanent magnet 168 is attached to the mounting ring 166, such as by gluing with suitable adhesive, and surrounds the moving coil 158. The fixed magnet is provided with a north/south magnetic polarity at its opposite ends as shown in FIG. 13. As a result, when an output signal is transmitted from the amplifier in the main housing (not shown) through leads 78 and 80 to the coil 156, the resulting magnetic field moves such coil, the core 158 and coupling rod 160 as a unit relative to the fixed magnet 168 to deflect the mounting diaphragms 162 and 164. Since the coupling rod 160 is made of ferromagnetic material, such as steel, it is held in engagement with the contact element 38 of FIG. 2 and 3 due to the magnet insert 142 in such contact element.

An electrical contact 170 is supported in spaced alignment with the coupling rod 160 on a rigid plastic support member 172 of generally U-shape which is fixedly secured to the mounting ring 166 in position so that such contact is engaged by the upper end of the output coupling rod 160 when such coupling rod is deflected through too great an amplitude. A first electrical lead 174 is connected to the contact 170 and a second lead 176 is connected to coupling rod 160 so that when such rod engages such contact an electrical circuit will be closed to produce an indicating signal which is transmitted through the amplifier 18 (not shown) to indicate to the hearing aid wearer that static inward pressure on the coupling element exists and the position of the hearing aid in the canal should be changed to relieve such pressure. It should be noted that each of the diaphragms 162 and 164 is provided with a plurality of vent holes 178 to allow air to pass therethrough for more easier deflection of the diaphragms in a similar manner to the embodiments of FIGS. 9 to 11. Also, the flexible output housing 26' shown in phantom lines, encloses the modified output transducer 132 of FIGS. 12 and 13 and is glued to the main housing 15 (not shown) in a similar manner to that of the embodiment of FIGS. 10 and 11, but this has not been shown. Of course, a pair of central holes are also provided in the diaphragms 162 and 164 to allow the coupling rod 160 to extend therethrough, such coupling rod moving with the diaphragms during deflection. It should be noted that the electrical contact 170 mounted on the support 172 also functions as a stop to prevent overstressing of the diaphragms 162 and 164, since it limits the deflection of such diaphragms by engagement with the coupling rod 160.

Figure 14:
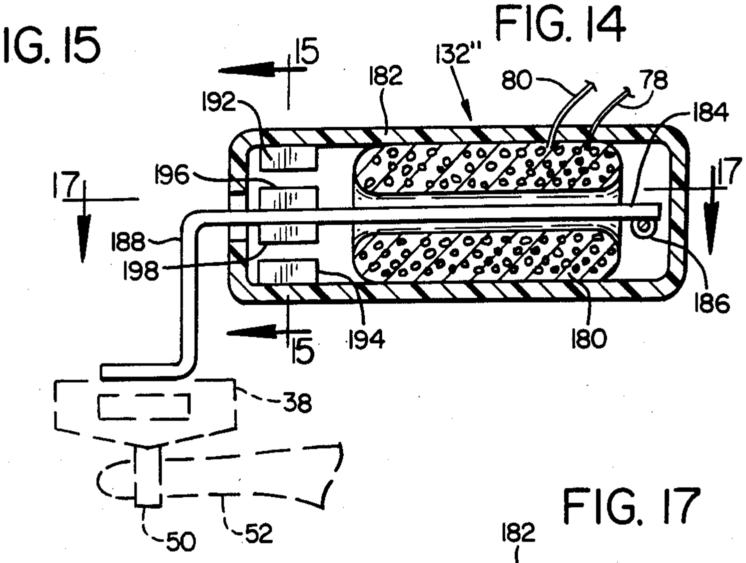
FIG. 14 is a partial section view of a fifth embodiment of the invention having an electromagnetic output transducer with a pivoted motor member resiliently suspended by permanent magnets and deflected by an electromagnetic coil so that the output coupling element on the end of such motor member provides movement to the contact element.
Figure 17:
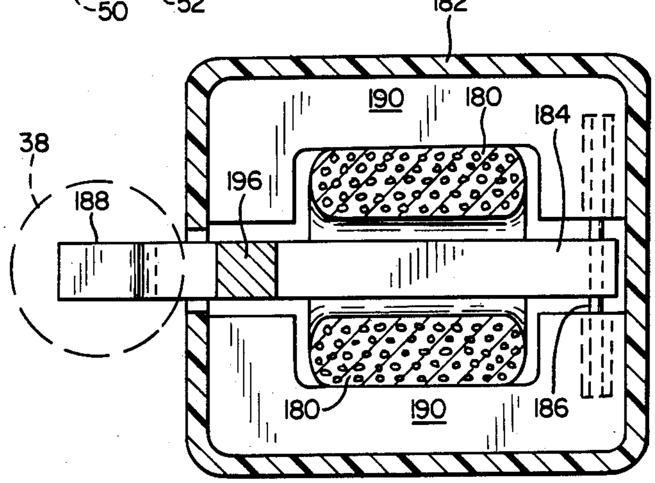
FIG. 17 is a horizontal section view taken along the line 17—17 of FIG. 14.

A fifth embodiment of the hearing aid of the present invention is shown in FIGS. 14 to 17 which employs an electromagnetic output transducer 132" of a different type from that previously described. Transducer 132" includes an electromagnetic coil 180 which is fixedly secured to the inside of a rigid plastic shell 182 containing such transducer. A motor member or armature 184 of ferromagnetic material, such as steel, is pivotally mounted at one end for pivoting movement about a hinge 186 and extends through the coil 180. The free end of the motor member 182 is bent perpendicularly downward and extends out through an opening in the front end of the plastic shell 182 to form an output coupling element 188. The end of this coupling element is bent perpendicularly to extend outward and held in engagement with the contact element 38 mounted on the surface of the tympanic membrane, as shown in FIG. 14.

A pair of lateral magnetic core arms 190 of ferromagnetic material are fixedly supported on the side walls of the plastic shell 182 around the coil 180 on opposite sides of the motor member 184. The ends of the core arms 190 are spaced by air gaps from the hinge end of the motor member 184 and the junction of such motor member with the coupling element 188. As a result, when the output signal of the amplifier transmitted through leads 78 and 80 is applied to the electromagnetic coil 180, such coil induces a magnetic field in the motor member 184 causing it to pivot about hinge 186 up and down due to attraction and repulsion of the stator magnets 192 and 194, thereby transmitting mechanical movement through the coupling element 188 to the contact element 38. It should be noted that the motor member 184 is mounted by hinge 186 on the fixed lateral arm members 190 in any suitable manner, such as by a rotatable pin, which pivots within two hollow metal tubes welded to the lateral arms and is fixed, such as by welding, to similar tubing attached to the motor member or armature 184.

Figure 15:
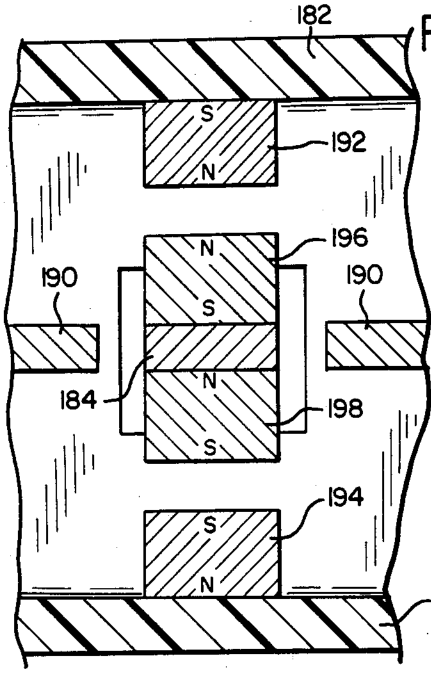
FIG. 15 is an enlarged vertical section view taken along the line 15—15 of FIG. 14.
Figure 16:
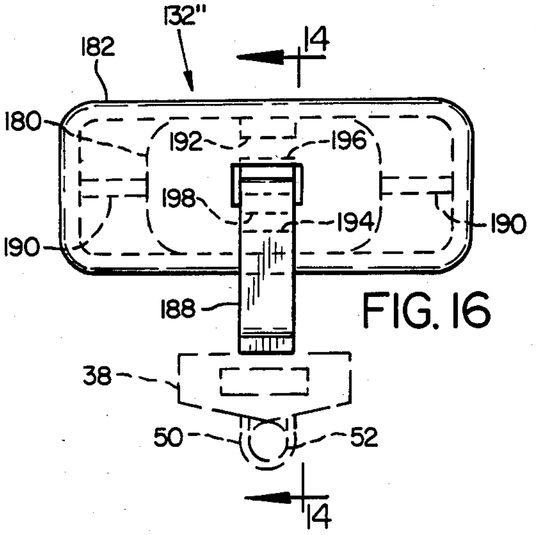
FIG. 16 is a front elevation view taken along the line 16—16 of FIG. 14.

A permanent magnet suspension system is provided for supporting the motor member 184 in a quiescent horizontal position. The magnetic suspension system is shown in FIG. 15 and includes a pair of fixed permanent magnets 192 and 194 which are attached by glue to the plastic shell 182 on opposite sides of the motor member. A pair of movable permanent magnets 196 and 198 are glued to the opposite sides of the motor member 184 in a position so that such motor magnets are aligned with the fixed stator magnets 192 and 194. The magnetic polarity of the stator magnets 192 and 194 and the motor magnets 196 and 198 are opposite as shown in FIG. 15 so that the stator magnets repel the motor magnets and hold the motor member 184 spaced vertically from the stator magnets in the quiescent position shown. It should be noted that in this quiescent position, the motor member 184 is in horizontal alignment with the lateral core arms 190, but is spaced horizontally by air gaps therefrom. When a signal is applied to the coil 180, an electromagnetic field is also produced in the lateral arms 190 which operates on the motor magnets 196 and 198 to deflect the motor member 184 vertically up and down from the position shown in FIG. 15. The advantage of this magnetic suspension is that the motor element is caused to "float" so it is of a high deflection resiliency. Also, the thickness of the output transducer 132 is greatly reduced as shown in FIG. 16 by the short height of the shell 182, for more easier insertion within the ear canal into a position so that the coupling element 188 contacts the contact element 38 mounted on the tympanic membrane. It should be noted that a similar type of magnetic suspension can be employed on a piezoelectric output transducer.

It will be obvious to those having ordinary skill in the art that many changes may be made in the above described preferred embodiments of the present invention. Therefore, the scope of the present invention should only be determined by the following claims.

I claim:

1. Hearing aid apparatus adapted for mounting within the ear canal to provide direct coupling through the tympanic membrane, comprising:

an input transducer means for converting sound waves to electrical input signals of audio frequency;

amplifier means for amplifying said input signals applied to an input of said amplifier means to produce amplified electrical output signals at an ouput of said amplifier means;

D.C. voltage power supply means for said amplifier means including battery means;

an output transducer means for converting received signals corresponding to said output signals into mechanical movement of an output coupling element of said transducer means without the production of perceptible sound waves;

mounting means for removably mounting said output transducer means in the ear canal external to the tympanic membrane; and support means for supporting said coupling element in engagement with a contact element mounted on the outer surface of the tympanic membrane by a clip means for attachment to the malleus bone of the ear by a pair of clamp arms extending through the tympanic membrane so that there is no air gap between said coupling element and the tympanic membrane, and to provide direct electromechanical coupling from the output transducer means to the ossicle bones within the ear through the tympanic membrane in response to the movement of said coupling element.

2. Hearing aid apparatus in accordance with claim 1 in which the contact element mounted on the outer surface of the tympanic membrane is magnetically attached to said coupling element.

3. Hearing aid apparatus in accordance with claim 2 in which said clip means is metal.

4. Hearing aid apparatus in accordance with claim 2 in which the contact element includes a magnetic member for facilitating said engagement with said coupling element.

5. Hearing aid apparatus in accordance with claim 4 in which the magnetic member is a permanent magnet.

6. Hearing aid apparatus in accordance with claim 1 in which the output transducer means is an electromagnetic transducer means for producing an electromagnetic field in response to said output signals to move a coupling element of magnetic material.

7. Hearing aid apparatus in accordance with claim 6 in which electromagnetic output transducer means includes a pair of spaced flexible diaphragms of non-magnetic material between which an electromagnetic coil is mounted for movement therewith, an annular permanent magnet fixedly mounted between said diaphragms in a position surrounding and separated from said coil, and the coupling element is secured to said diaphragms in the center of said coil for movement therewith so that one end of said coupling element extends through one of the diaphragms to engage a contact element on the outer surface of the tympanic membrane.

8. Hearing aid apparatus in accordance with claim 6 in which the electromagnetic output transducer has a motor element supported for movement by a pair of spaced flexible resilient suspension means of non-magnetic material which are coupled together for simultaneous movement in response to the application of said output signals to an electromagnetic coil, said motor element being connected to said coupling element for movement therewith.

9. Hearing aid apparatus in accordance with claim 1 in which the coupling element is provided by a motor member which is pivotally mounted and is supported by permanent magnet suspension means.

10. Hearing aid apparatus in accordance with claim 9 in which the output transducer is an electromagnetic transducer which includes a motor member of magnetic material pivotally mounted at one end thereof with its other end attached to the output coupling element and having first permanent magnet means mounted thereon and includes a pair of second permanent magnets fixedly mounted above and below the first magnet means with a magnetic polarity so that the first magnet means is repelled by and suspended by the magnetic field between said pair of second magnets, a pair of stator members of magnetic material on opposite sides of the motor member, and electromagnetic coil means surrounding the motor member to which the output signals are applied for deflecting the motor member and coupling element.

11. Hearing aid apparatus in accordance with claim 1 in which the output transducer means includes a piezoelectric means for moving said coupling element in response to said output signals.

12. Hearing aid apparatus in accordance with claim 11 in which the piezoelectric means comprises piezoelectric plastic film.

13. Hearing aid apparatus in accordance with claim 12 in which the piezoelectric plastic film is made of polyvinylidene fluoride.

14. Hearing aid apparatus in accordance with claim 1 which also includes counterpoise means coupled to the output transducer means, which moves in an opposite direction to the coupling element to reduce vibration of said apparatus.

15. Hearing aid apparatus in accordance with claim 1 in which the coupling element engages an electrical contact on a stop plate to produce an indicator signal when there is excessive deflection of said coupling element.

* * * * *

UNITED STATES PATENT AND TRADEMARK OFFICE

CERTIFICATE OF CORRECTION

PATENT NO. : 4,628,907

DATED : December 16, 1986

INVENTOR(S) : JOHN M. EPLEY

It is certified that error appears in the above-identified patent and that said Letters Patent is hereby corrected as shown below:

Title Page: References Cited:

Under Other Publications, "Arch Otolarngol" should be --Arch Otolaryngol--.

Column 2, line 25, "undirectional" should be --unidirectional--.

Column 2, line 42, "undirectional" should be --unidirectional--.

Column 3, line 24, "previous" should be --previously--.

Column 7, line 56, "visa versa" should be --vice versa--.

Column 10, line 3, "orientated" should be --oriented--.

Column 11, line 22, "and are" should be --and they are--.

Column 12, line 46, "more easier" should be --easier--.

Column 13, line 60, "more easier" should be --easier--.

Signed and Sealed this

Thirteenth Day of July, 1993

Attest:

Michael K. Kirk

MICHAEL K. KIRK

*Attesting Officer* *Acting Commissioner of Patents and Trademarks*